(12) United States Patent
Yaku et al.

(10) Patent No.: US 10,294,521 B2
(45) Date of Patent: May 21, 2019

(54) METHOD OF EXTENDING DNA WITH TELOMERASE AND METHOD OF MEASURING TELOMERASE ACTIVITY

(71) Applicant: Panasonic Corporation, Osaka (JP)

(72) Inventors: Hidenobu Yaku, Hyogo (JP); Daisuke Miyoshi, Kyoto (JP)

(73) Assignee: Panasonic Corporation, Osaka (JP)

( * ) Notice: Subject to any disclaimer, the term of this patent is extended or adjusted under 35 U.S.C. 154(b) by 520 days.

(21) Appl. No.: 14/743,901

(22) Filed: Jun. 18, 2015

(65) Prior Publication Data

US 2015/0322501 A1    Nov. 12, 2015

Related U.S. Application Data

(63) Continuation of application No. PCT/JP2014/004080, filed on Aug. 5, 2014.

(30) Foreign Application Priority Data

Aug. 29, 2013 (JP) .................................. 2013-177846

(51) Int. Cl.
    *C12P 19/34*  (2006.01)
    *C12Q 1/6844* (2018.01)
    *C12Q 1/48*   (2006.01)
    *C12Q 1/686*  (2018.01)

(52) U.S. Cl.
    CPC ............. *C12Q 1/6844* (2013.01); *C12Q 1/48* (2013.01); *C12Q 1/686* (2013.01); *G01N 2333/9128* (2013.01)

(58) Field of Classification Search
    USPC ...................................... 435/6.12, 91.1, 91.2
    See application file for complete search history.

(56) References Cited

U.S. PATENT DOCUMENTS 6,995,145 B1 * 2/2006 Au .......................... A61K 31/70
                                                     514/42
8,101,357 B2   1/2012 Yaku et al.

2010/0261246 A1  10/2010 Yaku et al.
2010/0292197 A1  11/2010 Harley et al.
2014/0088055 A1   3/2014 Harley et al.

FOREIGN PATENT DOCUMENTS

| JP | 9-206081    | 8/1997  |
| JP | 2004-261062 | 9/2004  |
| JP | 2012-532092 | 12/2012 |
| WO | 2010/116423 | 10/2010 |

OTHER PUBLICATIONS

International Search Report of PCT application No. PCT/JP2014/004080 dated Nov. 4, 2014.
Ran Chen et al, "Premature termination of telomeric extension-PCR for detection of telomerase activity" Biotechniques, vol. 35, No. 1, Jul. 2003, pp. 158-162.
Nam W. Kim, et al., "Specific Association of Human Telomerase Activity with Immortal Cells and Cancer", Science, vol. 266, Dec. 23, 1994, pp. 2011-2015.
Hidenobu Yaku, et al., "Anionic phthalocyanines targeting G-quadruplexes and inhibiting telomerase activity in the presence of excessive DNA duplexes", Chem. Commun., 2010, 46, pp. 5740-5742.
Schmidt, P.M et al., "Detection of activity of telomerase in tumor cells using fiber optical biosensors" Biosensors and Bioelectronics17(2002) pp. 1081-1087.
Grimm, J. et al., "Novel nanosensors for rapid analysis of telomerase activity" Cancer Research 64, Jan. 15, 2004, pp. 639-643.

* cited by examiner

*Primary Examiner* — Kenneth R Horlick
(74) *Attorney, Agent, or Firm* — McDermott Will & Emery LLP (57) ABSTRACT

The present disclosure provides a measurement method of telomerase activity with no occurrence of false-negative and high quantitative capability. In the measurement method of telomerase activity of the present disclosure, a solution containing telomerase as a sample solution is mixed with a solution containing primer DNA as a substrate for telomerase even as or after a solution containing non-primer DNA not as a substrate for telomerase is mixed therewith. Non-primer DNA can remove an effect of DNase in the sample solution and prevent occurrence of false-negative. Subsequently, the primer DNA is extended with the telomerase and the extended primer DNA is detected, through which telomerase activity is measured.

9 Claims, 8 Drawing Sheets

Specification includes a Sequence Listing.

METHOD OF EXTENDING DNA WITH TELOMERASE AND METHOD OF MEASURING TELOMERASE ACTIVITY

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

The material contained in the ASCII text filed named "P669164-02_Sequence_List" created on Jun. 18, 2015 and having a file size of 678 bytes is incorporated herein by reference.

BACKGROUND

1. Field of the Invention

The present disclosure relates to a measurement method of telomerase activity.

2. Description of the Related Art

One example of measurement methods of telomerase activity includes Telomere Repeat Amplification Protocol assay (hereinafter, referred to as TRAP assay) (NPL 1). TRAP assay is conducted according to the following procedure.

1. Telomerase reaction is carried out with telomerase in a biological sample lysis solution.
2. The telomerase reaction products obtained in the step 1 are amplified by PCR and then the amplified products are analyzed by electrophoresis.

A research has been reported that to evaluate inhibitory effect of a telomerase inhibitor in a cell nucleus, λDNA which is simulated as genomic DNA is added to a telomerase reaction solution to construct a pseudo-cell nucleus environment (NPL 2).

CITATION LIST

Patent Literature

PTL 1: U.S. Pat. No. 8,101,357 (esp. col. 10, line 36 to col. 11, line 25) Non-Patent Literatures NPL 1: Nam W. Kim, et al., "Specific Association of Human Telomerase Activity with Immortal Cells and Cancer", Science, vol. 266, 1994, pp. 2011-2015

NPL 2: Hidenobu Yaku, et al., "Anionic phthalocyanines targeting G-quadruplexes and inhibiting telomerase activity in the presence of excessive DNA duplexes", Chem. Commun., 2010, 46, 5740-5742

NPL 3: Schmidt, P. M.; Lehmann, C.; Matthes, E.; Bier, F. F. Detection of activity of telomerase in tumor cells using fiber optical biosensors. Biosens. Bioelectron. 2002, 17, 1081-1087.

NPL 4: Grimm, J.; Perez, J. M.; Josephson, L.; Weissleder, R. Novel nanosensors for rapid analysis of telomerase activity. Cancer Res. 2004, 64, (2), 639-643.

SUMMARY

The demand has been expected to have a measurement method of telomerase activity with higher accuracy than the methods disclosed in NPLs 1 and 2. An object of the present disclosure is to provide a novel measurement method of telomerase activity, the method having higher accuracy compared to conventional measurement methods of telomerase activity.

A first aspect of the present disclosure is a measurement method of telomerase activity for measuring an activity of telomerase, the method including the steps of:

(a) preparing a first mixed solution of a telomerase-containing solution with a solution containing non-primer DNA not as a substrate for telomerase;

(b) mixing the first mixed solution with a solution containing primer DNA as a substrate for telomerase after the step (a);

(c) extending the primer DNA with the telomerase after the step (b); and (d) detecting the extended primer DNA after the step (c).

The step (d) preferably includes the steps of:

(e) amplifying the extended primer DNA by PCR;

(f) subjecting the amplified DNA products obtained by the PCR to electrophoresis; and (g) assessing the result from the electrophoresis.

A second aspect of the present disclosure is a measurement method of telomerase activity for measuring an activity of telomerase, the method including the steps of:

(h) preparing a second mixed solution of a solution containing primer DNA as a substrate for telomerase with a solution containing non-primer DNA not as a substrate for telomerase;

(i) mixing the second mixed solution with a telomerase-containing solution after the step (h);

(j) extending the primer DNA with the telomerase after the step (i); and (k) detecting the extended primer DNA after the step (j).

The step (k) preferably includes the steps of:

(l) amplifying the extended primer DNA by PCR;

(m) subjecting the amplified DNA products obtained by the PCR to electrophoresis; and (n) assessing the result from electrophoresis.

The non-primer DNA is preferably one not complementary to the base sequence (5'-CUAACCCUAAC-3': SEQ ID NO: 1) at positions between 46 and 56 in telomerase RNA.

The non-primer DNA is more preferably λDNA, plasmid DNA or M13DNA.

The non-primer DNA is still more preferably plasmid DNA or M13DNA.

A third aspect of the present disclosure is a method for extending primer DNA with telomerase, the method including the following steps of:

(a) mixing non-primer DNA not as a substrate for telomerase with a solution containing telomerase and DNase to provide a mixed solution; and (b) extending primer DNA with the telomerase by adding primer DNA as a substrate for telomerase to the mixed solution during degradation of the non-primer DNA with the DNase after the step (a).

The non-primer DNA is preferably λDNA, plasmid DNA or M13DNA.

A fourth aspect of the present disclosure is a method for measuring an activity degree of telomerase, the method including the following steps of:

(a) mixing a solution containing telomerase and DNase with non-primer DNA not as a substrate for telomerase to provide a mixed solution;

(b) extending primer DNA with the telomerase by adding primer DNA as a substrate for telomerase to the mixed solution during degradation of the non-primer DNA with the DNase after the step (a); and (c) determining an activity of the telomerase based on an extension degree of the extended primer DNA in the step (b).

The step (c) preferably includes the steps of:

(c1) amplifying the extended primer DNA in the step (b) by PCR;

(c2) subjecting the amplified primer DNA in the step (c1) to electrophoresis; and (c3) determining an activity degree of the telomerase based on the result from electrophoresis in the step (c2).

The non-primer DNA is preferably λDNA, plasmid DNA or M13DNA.

A fifth aspect of the present disclosure is a method for extending primer DNA with telomerase, the method including the following steps of:

(a) preparing a mixed solution containing non-primer DNA not as a substrate for telomerase and primer DNA as a substrate for telomerase; and (b) extending the primer DNA with the telomerase by adding a solution containing telomerase and DNase to the mixed solution while degrading the non-primer DNA with the DNase after the step (a).

The non-primer DNA is preferably λDNA, plasmid DNA or M13DNA.

A sixth aspect of the present disclosure is a method for measuring an activity degree of telomerase, the method including the following steps of:

(a) preparing a mixed solution containing non-primer DNA not as a substrate for telomerase and primer DNA as a substrate for telomerase;

(b) extending the primer DNA with the telomerase by adding a solution containing telomerase and DNase to the mixed solution while degrading the non-primer DNA with the DNase after the step (a); and (c) determining an activity of the telomerase based on an extension degree of the extended primer DNA in the step (b).

The step (c) preferably includes the steps of:

(c1) amplifying the extended primer DNA in the step (b) by PCR;

(c2) subjecting the amplified primer DNA in the step (c1) to electrophoresis;

and (c3) determining an activity degree of the telomerase based on the result from electrophoresis in the step (c2).

The non-primer DNA is preferably λDNA, plasmid DNA or M13DNA.

The present disclosure can measure telomerase activity in higher accurate manner compared to conventional measurement methods.

DETAILED DESCRIPTION OF THE EMBODIMENTS

A first aspect of the present disclosure relates to a measurement method of telomerase activity for measuring an activity of telomerase, the method including the steps of:

(a) preparing a first mixed solution of a telomerase-containing solution with a solution containing non-primer DNA not as a substrate for telomerase;

(b) mixing the first mixed solution with a solution containing primer DNA as a substrate for telomerase after the step (a);

(c) extending the primer DNA with the telomerase after the step (b); and (d) detecting the extended primer DNA after the step (c).

A second aspect of the present disclosure relates to a measurement method of telomerase activity for measuring activity of telomerase, the method including the steps of:

(h) preparing a second mixed solution of a solution containing primer DNA as a substrate for telomerase with a solution containing non-primer DNA not as a substrate for telomerase;

(i) mixing the second mixed solution with a telomerase-containing solution after the step (h);

(j) extending the primer DNA with the telomerase after the step (i); and (k) detecting the extended primer DNA after the step (j).

A third aspect of the present disclosure is a method for extending primer DNA with telomerase, the method including the following steps of:

(a) mixing a non-primer DNA not as a substrate for telomerase with a solution containing telomerase and DNase to provide a mixed solution; and (b) extending primer DNA with the telomerase by adding primer DNA as a substrate for telomerase to the mixed solution during degradation of the non-primer DNA with the DNase after the step (a).

A fourth aspect of the present disclosure is a method for measuring an activity degree of telomerase, the method including the following steps of:

(a) mixing a solution containing telomerase and DNase with non-primer DNA not as a substrate for telomerase to provide a mixed solution;

(b) extending primer DNA with the telomerase by adding primer DNA as a substrate for telomerase to the mixed solution during degradation of the non-primer DNA with the DNase after the step (a); and (c) determining an activity of the telomerase based on an extension degree of the extended primer DNA in the step (b).

A fifth aspect of the present disclosure is a method for extending primer DNA with telomerase, the method including the following steps of:

(a) preparing a mixed solution containing non-primer DNA not as a substrate for telomerase and primer DNA as a substrate for telomerase; and (b) extending the primer DNA with the telomerase by adding a solution containing telomerase and DNase to the mixed solution while degrading the non-primer DNA with the DNase after the step (a).

A sixth aspect of the present disclosure is a method for measuring an activity degree of telomerase, the method including the following steps of:

(a) preparing a mixed solution containing non-primer DNA not as a substrate for telomerase and primer DNA as a substrate for telomerase;

(b) extending the primer DNA with the telomerase by adding a solution containing telomerase and DNase to the mixed solution while degrading the non-primer DNA with the DNase after the step (a); and (c) determining an activity of the telomerase based on an extension degree of the extended primer DNA in the step (b).

BACKGROUND TO DEVELOPMENT OF THE PRESENT DISCLOSURE

In a normal somatic cell, telomeric DNA is shortened at every round of cell division, and the cell division is arrested after repeating at certain rounds. In contrast, in a cancer cell, telomerase is activated and its telomeric DNA does not arrest a reaction for extending DNA and continues to repeat the reaction, resulting in immortal proliferation of cells. Measurement of telomerase activity can be one of useful test techniques for cancer diagnosis and therefore the measurement has been received much attention.

Conventional measurement methods of telomerase activity, as disclosed in NPL 1 or 2, have a basic mechanism that telomerase in a cell lysis solution is allowed to react a TS primer (primer DNA as a substrate for telomerase), the reaction products obtained by the telomerase reaction (a reaction for extending telomeric DNA), DNA fragments are amplified by PCR and the DNA fragment is detected by electrophoresis. A sample solution for measuring telomerase activity is a solution obtained by dissolving a biological sample such as a cell in a surfactant or a cytolytic buffer containing a surfactant, or by fragmenting a biological sample such as a cell in a solution by physical means of homogenization or ultrasonic oscillation.

There is to be expected that the higher telomerase concentration a sample has, the stronger intensity of a ladder of bands widely appears with by electrophoresis. However, in a sample with high telomerase concentration, the ladder of bands is known to appear with weaker intensity compared to that of a sample with low telomerase concentration or appear merely in a narrow range, in some cases. That is, a conventional measurement method for telomerase activity is problematic in that it has low sensitivity and sometimes provides occurrence of false-negative.

In sample solutions, non-primer DNA not as a substrate for telomerase is also contained. The present inventors have studied an effect of λDNA on measurement of telomerase activity in conventional methods as disclosed in NPL 2, where the λDNA, which is contained in a sample, is added to a reaction system as non-primer DNA not as a substrate for telomerase derived from a cell. Consequently, there is found that addition of λDNA is not obstructive of reaction of telomerase with a TS primer.

Accordingly, the present inventors have focused on the fact that the sample solution also contains an enzyme, deoxyribonuclease (DNase) which degrades DNA. The presence of DNase in a telomerase reaction system forcedly degrades DNA fragments, the reaction products from TS primer-telomerase reaction. Therefore, the present inventors have inferred that a sample solution containing DNase is mixed with primer DNA as a substrate for telomerase after non-primer DNA not as a substrate for telomerase is allowed to be present in a reaction system and thereby an effect of DNase is excluded, which is possible to improve sensitivity for measurement of telomerase activity and reduce occurrence of false-negative, and have accomplished the present disclosure.

Hereinafter, the exemplary embodiments of the present disclosure are described with reference to drawings.

First Exemplary Embodiment

Figure 1:
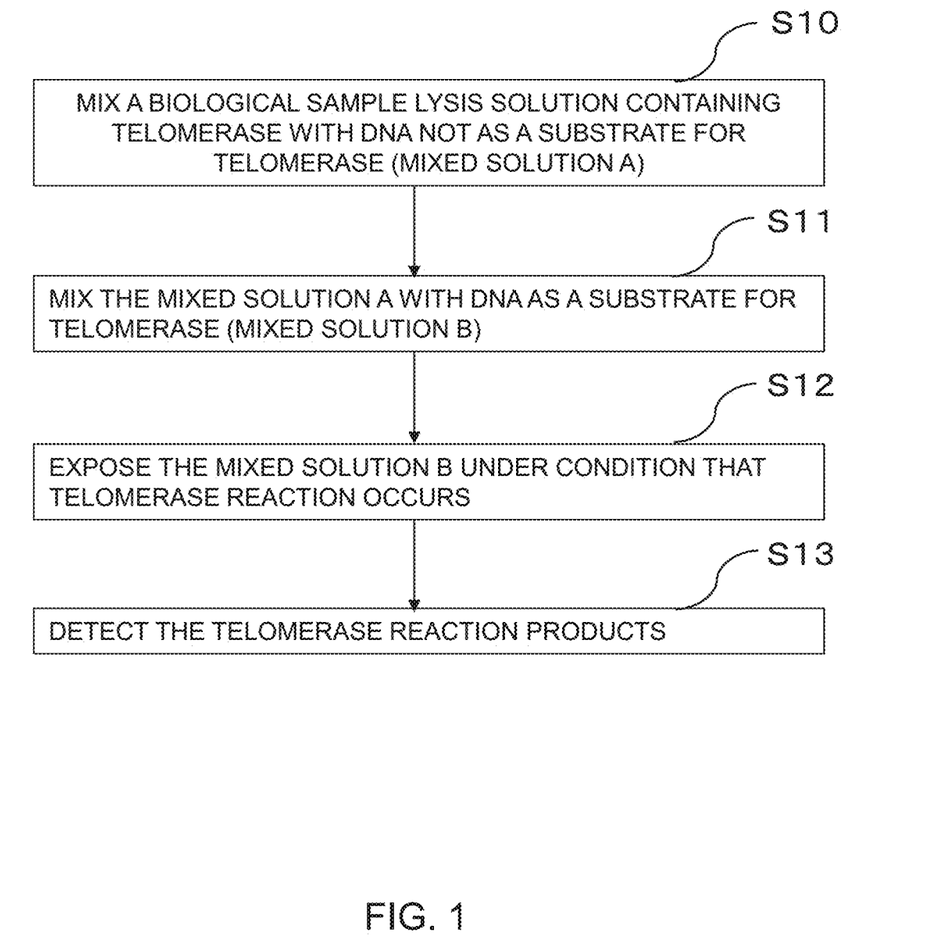
FIG. 1 shows a flow chart of the measurement method of telomerase activity according to the first aspect of the present disclosure.

FIG. 1 shows a flowchart of a measurement method of telomerase activity according to the first aspect of the present disclosure. Firstly, a biological sample solution containing telomerase is mixed with DNA not as a substrate for telomerase (non-primer DNA) to prepare a mixed solution A (first mixed solution) (Step S10). Herein, the term "biological sample solution" used in the present disclosure refers to a solution containing dissolved cells or biological tissue samples, or a solution corresponding to the same.

Examples of DNA not as a substrate for telomerase (non-primer DNA) include:
(i) λDNA,
(ii) plasmid DNA and
(iii) M13DNA.

(i) λDNA is linear double-stranded DNA. A typical λDNA has 48502 base pairs and is available from TAKARA BIO INC.

(ii) Plasmid DNA is composed of cyclic double-stranded DNA.

(iii) M13DNA is composed of cyclic single-stranded DNA.

As described above, examples of DNA not as a substrate for telomerase (non-primer DNA) include:
(i) linear double-stranded DNA
(ii) cyclic double-stranded DNA and
(iii) cyclic single-stranded DNA.

Secondly, the mixed solution A is mixed with DNA as a substrate for telomerase (primer DNA) to prepare a mixed solution B (Step S11). Herein, the term "DNA as a substrate for telomerase" used in the present disclosure refers to primer DNA which serves as a starting element of telomerase reaction. Particularly, the DNA refers to telomeric DNA, a TS primer (5'-AATCCGTCGAGCAGAGTT-3': SEQ ID NO: 2) or DNA corresponding to the same.

Subsequently, the mixed solution B is subjected to conditions where telomerase reaction occurs (Step S12). Particularly, the mixed solution B may be merely incubated at a temperature zone which allows the telomerase reaction to proceed. Specifically, incubation of the mixed solution B at around 30° C. to 40° C. allows the telomerase reaction to proceed effectively.

Then, the telomerase reaction products are detected (Step S13). Particularly, the telomerase reaction products (DNA fragments) are amplified by PCR, and the amplified products may be analyzed by electrophoresis. Detection methods of telomerase reaction products include, but are not limited to the combined method of PCR with electrophoresis, for example, a method in which optical fibers are employed (NPL 3) and a method in which magnetic resonance reader is employed (NPL 4), which can be employed herein.

The exemplary embodiment needs to contain at least Mg ion, deoxyadenosine triphosphate (hereinafter, referred to as dATP), deoxyguanosine triphosphate (hereinafter, referred to as dGTP) and deoxythymidine triphosphate (hereinafter, referred to as dTTP) in the mixed solution B. They may be added in any step before proceeding to Step S11.

In the exemplary embodiment, the telomerase reaction effectively proceeds in the mixed solution B containing a buffer component or a salt such as KCl. The salt can be also added in any step before proceeding to Step S11.

Through a set of the steps (Steps S10 to S13), measurement of telomerase activity can be made with no occurrence of false-negative and in a quantitative manner.

Second Exemplary Embodiment

Figure 2:
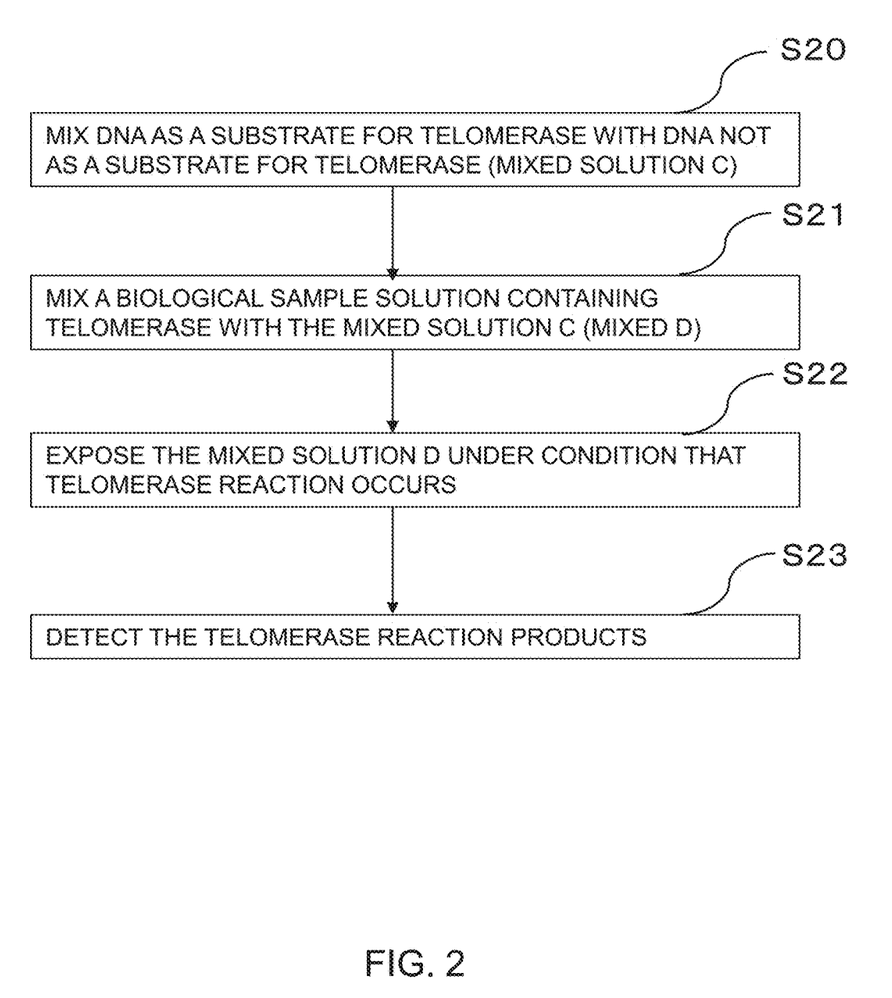
FIG. 2 shows a flow chart of the measurement method of telomerase activity according to the second aspect of the present disclosure.

FIG. 2 shows a flowchart of a measurement method of telomerase activity according to the second aspect of the present disclosure. The flowchart shown in FIG. 2 is the same as that of FIG. 1 except that a biological sample solution is mixed with DNA as a substrate for telomerase (primer DNA) after DNA not as a substrate for telomerase (non-primer DNA) is allowed to be present in the solution.

In the exemplary embodiment, DNA as a substrate for telomerase (primer DNA) is firstly mixed with DNA not as a substrate for telomerase (non-primer DNA) to prepare a mixed solution C (a second mixed solution) (Step S20).

Secondly, a biological sample solution containing telomerase is mixed with the mixed solution C to prepare a mixed solution D (Step S21).

Subsequently, the mixed solution D is subjected to conditions where telomerase reaction occurs (Step S22). Step S22 is the same step as Step S12 shown in FIG. 1.

Then, the telomerase reaction products are detected (Step S23). Step S23 is the same step as Step S13 shown in FIG. 1.

The exemplary embodiment also needs to contain at least Mg ion, deoxyadenosine triphosphate (hereinafter, referred to as dATP), deoxyguanosine triphosphate (hereinafter, referred to as dGTP) and deoxythymidine triphosphate (hereinafter, referred to as dTTP) in the mixed solution B. They may be added in any step before proceeding to Step 21.

Through a set of the steps (Steps S20 to S23), measurement of telomerase activity can be made with no occurrence of false-negative and in a quantitative manner.

Example 1/First Exemplary Embodiment

For a biological sample solution containing telomerase, used was a solution containing HeLa cells (available from Merk Millipore) lysed in CHAPS Lysis buffer (hereinafter, refer to as HeLa cell lysis solution). A HeLa cell is one of cancer cells and known to have activated telomerase within the cell. For DNA not as a substrate for telomerase, used was λDNA (available from TAKARA BIO INC.). λDNA is linear double-stranded DNA.

The experimental procedure of Example 1 is described below. Firstly, a mixed solution A1 as shown in Table 1 (first mixed solution) was prepared.

TABLE 1

| | |
|---|---|
| Buffer for telomerase reaction | 1 μL |
| dNTP mixed solution | 0.2 μL |
| 10 μM TS primer | 1 μL |
| 32 μg/mL λDNA | 2.6 μL |
| HeLa cell lysis solution | 2 μL |
| Water | 3.2 μL |
| Total volume | 10 μL |

For a buffer for telomerase reaction, used was 10×TRAP Reaction Buffer (incl. 200 mM Tris-HCl (pH 8.3), 15 mM $MgCl_2$, 630 mM KCl, 0.5% Tween20, and 10 mM EGTA) in TRAPEZE Telomerase Detection Kit (available from Merk Millipore). For a dNTP mixed solution, used was 50× dNTP Mix in TRAPEZE Telomerase Detection Kit (incl. dATP, dGTP, dTTP and dCTP, a concentration of 2.5 mM for each one). A TS primer was available from TSUKUBA OLIGO SERVICE CO., LTD. In the preparation of the mixed solution A, a TS primer was mixed with λDNA and then a HeLa cell lysis solution was added to and mixed with the mixture.

Subsequently, to allow the telomerase reaction to proceed in the mixed solution A1, the mixed solution A1 was incubated at 37° C. for 60 minutes.

Then, to terminate the telomerase reaction, the mixed solution A1 was incubated at 95° C. for 10 minutes, followed by being cooled to 4° C.

Next, to the mixed solution A1 was added water of 190 μl to obtain a mixed dilution A1.

Here, a mixed solution B1, as shown in Table 2, was prepared.

TABLE 2

| | |
|---|---|
| Buffer for PCR reaction | 1 μL |
| dNTP mixed solution | 0.2 μL |
| 10 μM TS primer | 1 μL |
| Primer mixed solution | 0.2 μL |
| Enzyme for PCR | 0.1 μL |
| Mixed dilution A1 | 4 μL |
| Water | 3.5 μL |
| Total volume | 10 μL |

For a buffer for PCR reaction, used was 10×LA PCR Buffer II ($Mg^{2+}$ plus) in TaKaRa LA Taq Hot Start Version (available from TAKARA BIO INC.). For a dNTP mixed solution, used was 50×dNTP Mix in TRAPEZE Telomerase Detection Kit. A TS primer was available from TSUKUBA OLIGO SERVICE CO., LTD. For a primer mixed solution, used was Primer Mix in TRAPEZE Telomerase Detection Kit. The Primer Mix contains a reverse primer for amplifying telomerase reaction products by PCR (TS primer for forward primer). For an enzyme for PCR, used was TaKaRa LA Taq HS in TaKaRa LA Taq Hot Start Version.

Subsequently, to amplify the telomerase reaction products by PCR, the mixed solution B was subjected to incubation of 30 cycles with one cycle of 95° C./30 sec, 59° C./30 sec, and 72° C./30 sec.

Then, the PCR products were subjected to polyacrylamide gel electrophoresis and analyzed. The gel used herein was a 10% polyacrylamide gel. The buffer used for the electrophoresis was Tris-Brate-EDTA buffer (hereinafter, referred to as "TBE buffer"). In the electrophoresis, a voltage was applied at 400 V.

Comparative Example 1

The experiment was carried out in the same manner as Example 1 except that λDNA was not used. The experimental procedure of Comparative Example 1 is described in details, below.

Firstly, a mixed solution A2, as shown in Table 3, was prepared.

TABLE 3

| | |
|---|---|
| Buffer for telomerase reaction | 1 μL |
| dNTP mixed solution | 0.2 μL |
| 10 μM TS primer | 1 μL |
| HeLa cell lysis solution | 2 μL |
| Water | 5.8 μL |
| Total volume | 10 μL |

Subsequently, in the mixed solution A2, telomerase reaction was carried out and then terminated. The experiment was carried out under the same conditions for telomerase reaction and termination as Example 1.

Then, the mixed solution A2 was cooled to 4° C.

Next, to the mixed solution A2 was added water of 190 μl to obtain a mixed dilution A2.

Here, a mixed solution B2, as shown in Table 4, was prepared.

TABLE 4

| Buffer for PCR reaction | 1 μL |
| --- | --- |
| dNTP mixed solution | 0.2 μL |
| 10 μM TS primer | 1 μL |
| Primer mixed solution | 0.2 μL |
| Enzyme for PCR | 0.1 μL |
| Mixed dilution A2 | 4 μL |
| Water | 3.5 μL |
| Total volume | 10 μL |

Subsequently, telomerase reaction products in the solution B2 were amplified by PCR. PCR was carried out under the same condition as Example 1.

Then, the PCR products were subjected to polyacrylamide gel electrophoresis and analyzed. Electrophoresis was carried out under the same condition as Example 1.

Figure 3A:
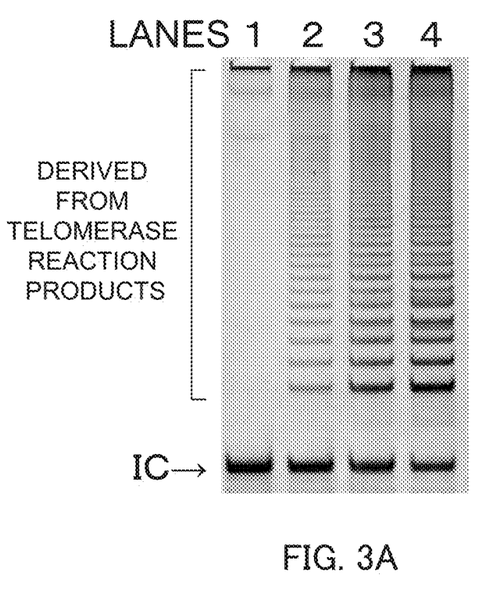
FIGS. 3A and 3B are photographic images each showing the results from electrophoresis in Example 1(a) and Comparative Example 1(b)
Figure 3B:
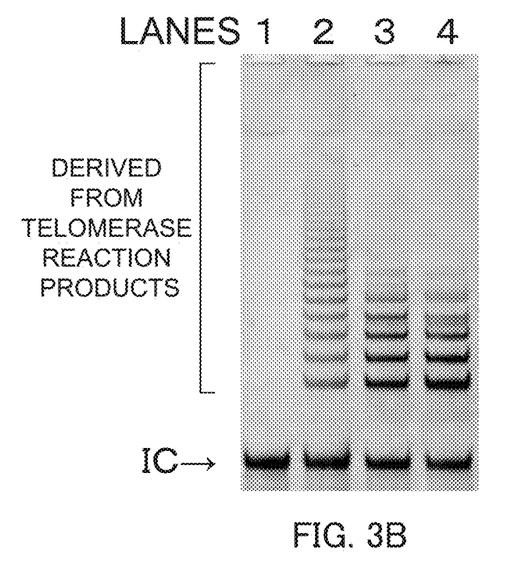

FIGS. 3A and 3B show the results from electrophoresis in Example 1 and Comparative Example 1, respectively. Ladders of bands in FIGS. 3A and 3B were derived from the telomerase reaction products. In FIGS. 3A and 3B, bands represented as "IC" (stands for Internal Control) were derived from the PCR products of template DNA contained in Primer Mix, the bands being telomerase reaction-independent. Therefore, IC bands were indicatives for confirming whether PCR was carried out or not.

In FIG. 3A, lanes 1, 2, 3 and 4 show the results from experiments that were made in the solutions A in Example 1, each of them containing HeLa cells of 0, 500, 2500 or 5000, respectively. FIG. 3A indicates that in Example 1, an amount of the telomerase reaction products increases with increased HeLa cells. Increased HeLa cells essentially lead to increased amount of telomerase, comprehensively resulting in increased amount of the telomerase reaction products. Thus, FIG. 3A indicates that telomerase activity in HeLa cells was accurately detected in Example 1.

In FIG. 3B, lanes 1, 2, 3 and 4 show the results from experiments that were made in the solutions A2 in Comparative Example 1, each of them containing HeLa cells of 0, 500, 2500 or 5000, respectively. As compared to lanes 2 to 4 in FIG. 3A, lanes 2 to 4 in FIG. 3B had less amounts of a long telomerase reaction products. Furthermore, FIG. 3B indicates that an amount of the long telomerase reaction products significantly decreases with increased HeLa cells. Increased HeLa cells should essentially lead to increased amount of the long telomerase reaction products, and therefore, FIG. 3B indicates that measurement of telomerase activity may provide occurrence of false-negative in Comparative Example 1.

IC bands in FIGS. 3A and 3B had almost similar intensities with each other. This indicates that differences of the results from electrophoresis found in Example 1 and Comparative Example 1 were not involved in PCR steps, but attributed to telomerase reaction steps. In other words, the differences mean that in Example 1, the telomerase reaction was normally carried out, whereas in Comparative Example 1, the telomerase reaction was not normally carried out.

Accordingly, in Example 1 and Comparative Example 1, PCR and electrophoresis were employed as a detection method of telomerase reaction products, however, even when other methods were employed to detect telomerase reaction products, comparable results should be achieved.

The above-mentioned results demonstrate that in the measurement method of telomerase activity according to the first aspect of the present disclosure, telomerase activity can be measured with no occurrence of false-negative.

Figure 4A:
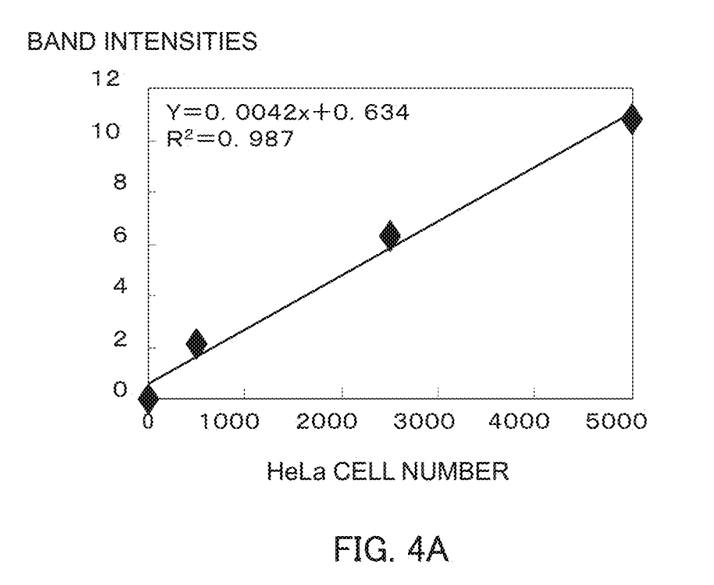
FIGS. 4A and 4B are graphs each showing a relationship between HeLa cell number and band intensity in Example 1(a) and Comparative Example 1(b)
Figure 4B:
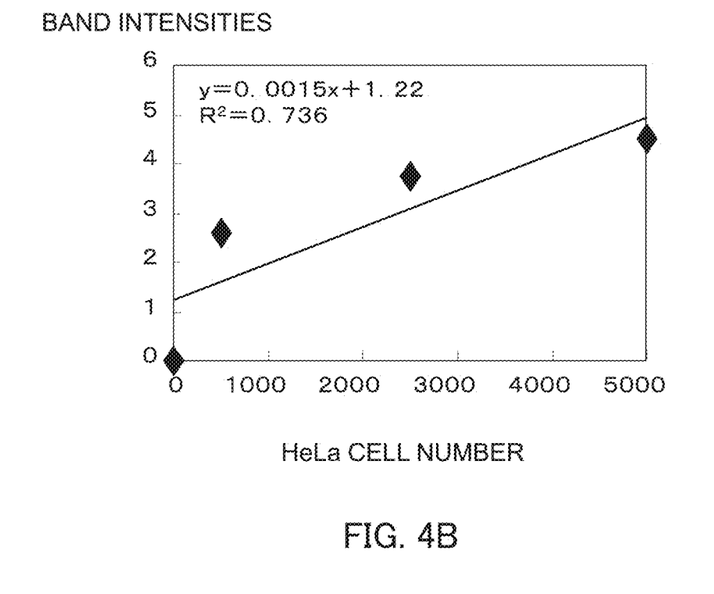

FIG. 4A shows a relationship between intensities of bands derived from the telomerase products in FIG. 3A and HeLa cell number. FIG. 4B shows a relationship between intensities of bands derived from the telomerase products in FIG. 3B and HeLa cell number. Comparison of these graphs with each other shows that Example 1 can detect HeLa cells with higher sensitivity than that of Example 2 under the same number of HeLa cells. Comparison of these graphs with each other shows that the measurement method in Example 1 has higher quantitative capability than that of Comparative Example 1.

The above-mentioned results demonstrated that in the measurement method of telomerase activity according to the first aspect of the present disclosure, telomerase activity in a cell can be measured with high sensitivity and high quantitative capability.

Example 2/Second Exemplary Embodiment

In preparation of a mixed solution A in Example 1, a TS primer was mixed with λDNA and then a HeLa cell lysis solution was added to and mixed with the mixture. Accordingly, the whole procedure was made in the same manner as Example 1 except that the HeLa cell lysis solution was mixed with λDNA and then the TS primer was added to and mixed with the mixture. Consequently, the same experimental result as Example 1 was obtained.

Comparative Example 2

In contrast to Example 2, a HeLa cell lysis solution was mixed with a TS primer and then λDNA was added to and mixed with the mixture, resulting in less amounts of telomerase reaction products.

Example 3/First Exemplary Embodiment

The whole procedure was made in the same manner as Example 1 except that plasmid DNA (pBR322: available from TAKARA BIO INC.) was used instead of λDNA. pBR322 is cyclic double-stranded DNA.

The experimental procedure of Example 3 is described in details, below.

Firstly, a mixed solution A3, as shown in Table 5, was prepared.

TABLE 5

| Buffer for telomerase reaction | 1 μL |
| --- | --- |
| dNTP mixed solution | 0.2 μL |
| 10 μM TS primer | 1 μL |
| 30 μg/mL pBR322 | 2.6 μL |
| HeLa cell lysis solution | 2 μL |
| Water | 3.2 μL |
| Total volume | 10 μL |

Subsequently, telomerase reaction was carried out in the mixed solution A3 and then terminated. The experiment was carried out under the same conditions for telomerase reaction and termination as Example 1.

Then, the mixed solution A3 was cooled to 4° C.

Next, to the mixed solution A3 was added water of 190 μL to obtain a mixed dilution A3.

Here, a mixed solution B3, as shown in Table 6, was prepared.

TABLE 6

| | |
|---|---|
| Buffer for PCR reaction | 1 μL |
| dNTP mixed solution | 0.2 μL |
| 10 μM TS primer | 1 μL |
| Primer mixed solution | 0.2 μL |
| Enzyme for PCR | 0.1 μL |
| Mixed dilution A3 | 4 μL |
| Water | 3.5 μL |
| Total volume | 10 μL |

Subsequently, telomerase reaction products in the solution B3 were amplified by PCR. PCR was carried out under the same condition as Example 1.

Then, the PCR products was subjected to polyacrylamide gel electrophoresis and analyzed. Electrophoresis was carried out under the same condition as Example 1.

Example 4/First Exemplary Embodiment

The whole procedure was made in the same manner as Example 3 except that DNA derived from M13 phage (hereinafter, referred to as M13DNA and available from New England Biolabs.) instead of λDNA. M13DNA is cyclic single-stranded DNA.

Figure 5A:
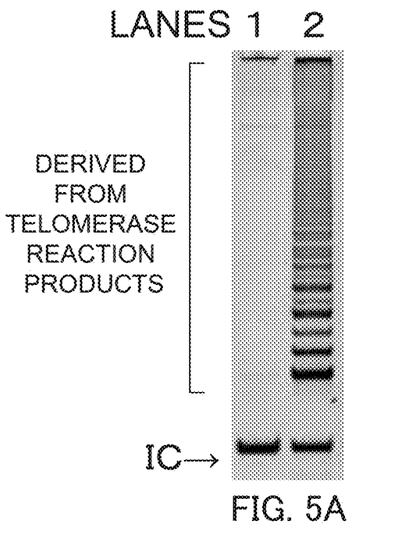
FIGS. 5A and 5B are photographic images each showing the results from electrophoresis in Examples 3 and 4.
Figure 5B:
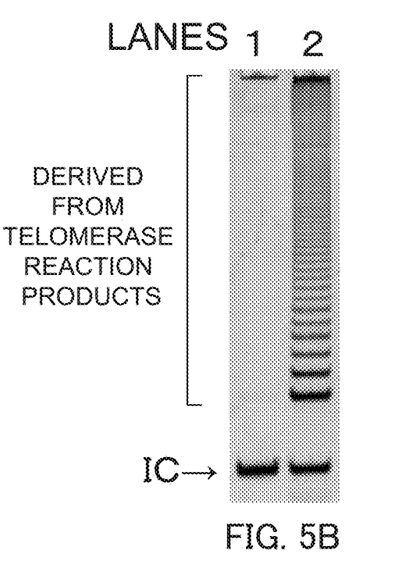

FIGS. 5A and 5B show the results from electrophoresis in Examples 3 and 4, respectively. Both of FIGS. 5A and 5B show the results of lane 1 where the HeLa cell count is 0 in the solution A3 and lane 2 where the HeLa cell count is 5000 in the solution A3.

From FIGS. 5A and 5B, even when any of pBR322 and M13DNA not as a substrate for telomerase was used, telomerase reaction products were not observed in the case of the HeLa cell count of 0. In contrast, the case of the HeLa cell count of 5000 gave the same result as lane 4 in FIG. 3A. These results indicate that the effect of λDNA, as observed in Example 1, was also found in both of pBR322 and M13DNA.

As described above, λDNA is linear double-stranded DNA, pBR322 is cyclic double-stranded DNA, and M13DNA is cyclic single-stranded DNA. Therefore, a term "DNA not as a substrate for telomerase" as used in the measurement method of telomerase activity according to the present disclosure may be in the linear or cyclic form. The term "DNA not as a substrate for telomerase" as used in the measurement method of telomerase activity according to the present disclosure may be single-stranded DNA or double-stranded DNA.

The term "DNA not as a substrate for telomerase" may be merely non-primer DNA that is not complementary to the base sequence at positions between 46 and 56 in telomerase RNA. There is considered that such DNA does not bind with telomerase, and does not serve as a starting element for telomerase reaction.

Example 5/Second Exemplary Embodiment

The whole procedure was made in the same manner as Example 2 except that pBR322 was used instead of λDNA. Consequently, the same experimental result as Examples 1 and 2 was obtained.

Example 5/Second Exemplary Embodiment

The whole procedure was made in the same manner as Example 2 except that M13DNA was used instead of λDNA. Consequently, the same experimental result as Examples 1 and 2 was obtained.

These results demonstrate that in the measurement method of telomerase activity according to the first and second aspects of the present disclosure, telomerase activity can be measured with no occurrence of false-negative and in a quantitative manner.

<Effect of Concentrations of DNA not as a Substrate for Telomerase>

In Example 1, the preparation of the mixed solution A1 was made with 32.0 μg/mL of λDNA, but the whole procedure was made in the same manner as Example 1 except that concentrations of λDNA used herein were varied in the range of 0, 1.06, 3.20, 10.6, 32.0, 106.0 and 320 μg/mL.

Figure 6:
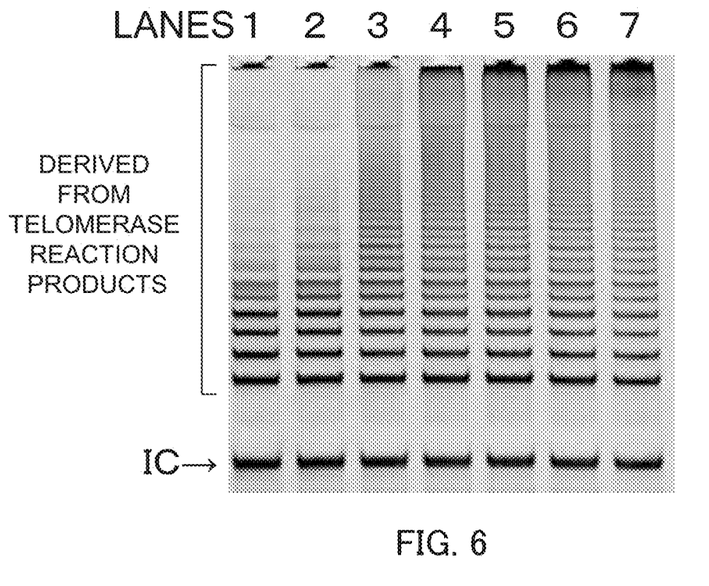
FIG. 6 is a photographic image showing the results from electrophoresis for λDNA with various concentrations in Example 1.

FIG. 6 shows the results from electrophoresis with various concentrations of λDNA in Example 1. In FIG. 6, lanes 1, 2, 3, 4, 5, 6 and 7 show the results of λDNA concentrations of 0, 1.06, 3.20, 10.6, 32.0, 106.0 and 320 μg/mL, at each of which λDNA was added to each mixed solution A1, respectively. Accordingly, in FIG. 6, lanes 1, 2, 3, 4, 5, 6 and 7 also show the results of λDNA concentrations of 0, 0.2756, 0.832, 2.756, 8.32, 27.56 and 83.2 μg/mL (final concentrations for reaction) in the mixed solution A1. The number of HeLa cells in the solution A1 was 5000, in all cases.

From the results of FIG. 6, long telomerase products were not observed in cases of 0 μg/mL and 0.2756 μg/mL of λDNA concentrations in the mixed solution A1. In contrast, in the case of 0.832 μg/mL of λDNA concentration in the mixed solution A1, long telomerase products were observed. These results demonstrate that when the concentration (final concentration) of λDNA in a telomerase reaction solution was 0.832 μg/mL or more, the occurrence of false-negative was not provided.

From the results in Examples 1 to 6, when concentrations of λDNA, pBR322 or M13DNA, which was added to telomerase reaction solutions, were comparable with one another, telomerase reaction products were obtained at comparable concentrations with one another. Thus, there is reasonably considered that when pBR322 or M13DNA is added to a telomerase reaction solution so as to be at 0.832 μg/mL or more, the occurrence of false-negative is not provided.

Example 7

Figure 7:
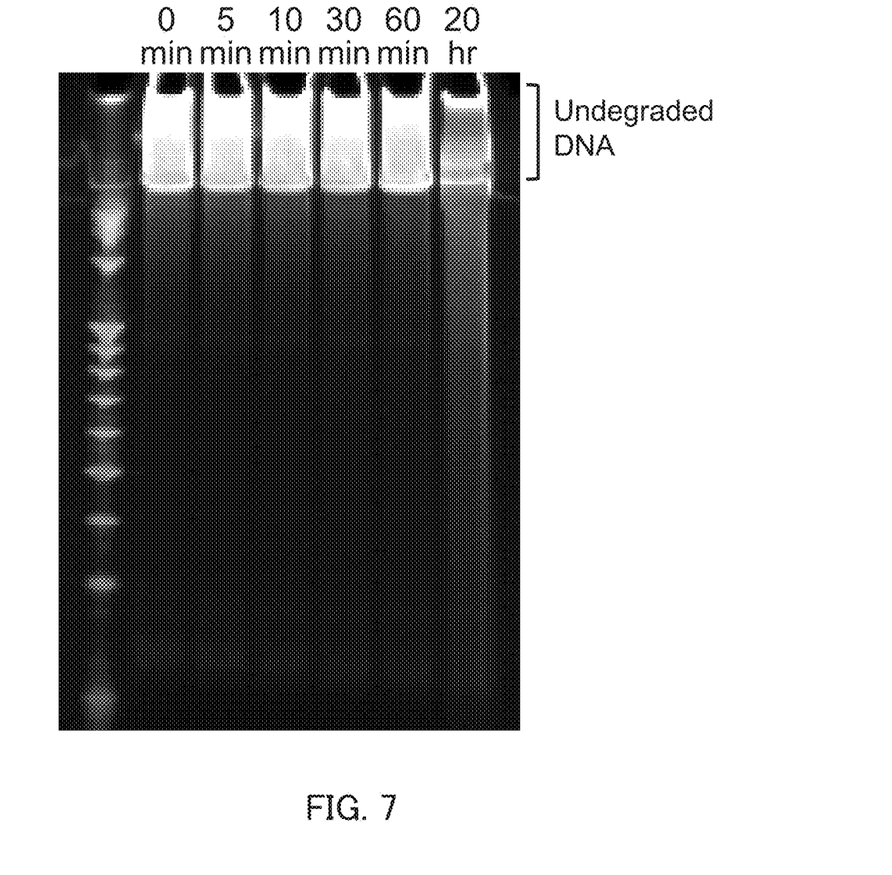
FIG. 7 is a photographic image showing the experimental result from electrophoresis in Example 7.
Figure 8:
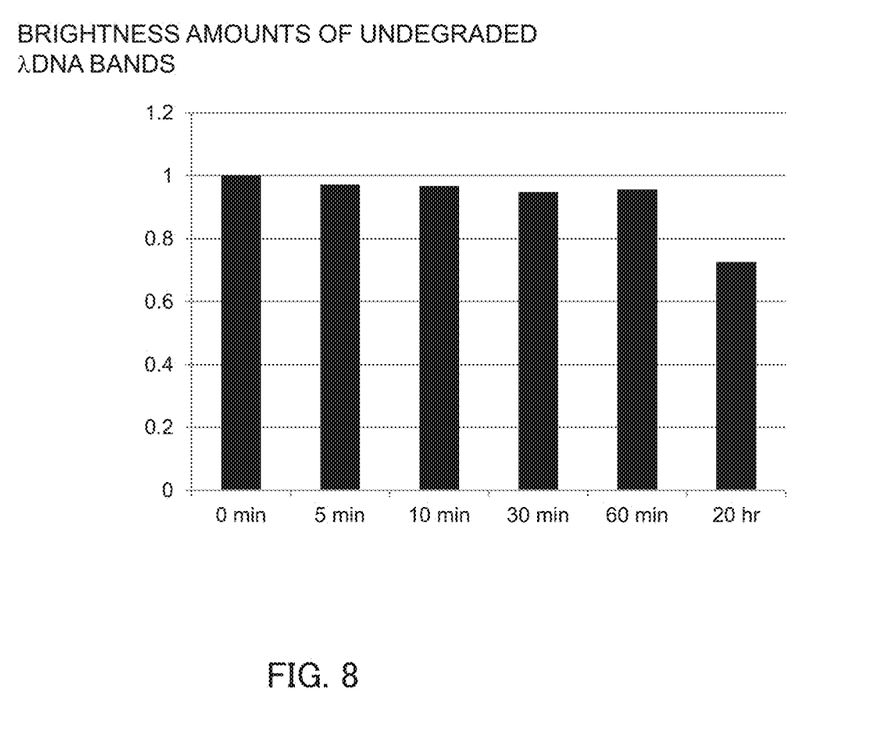
FIG. 8 is a graph showing a relationship between time amounts after incubation starts and brightness amounts of λDNA bands which are not degraded.

A reaction solution (100 μl) containing 200 mM Tris-HCl (pH 8.0), 40 mM $MgCl_2$, 320 μg/mL λDNA and HeLa cell lysis solution was incubated at 37° C. Then, the solution was taken out in each aliquot of 10 μl at 0, 5, 10, 30, 60 and 1200 minutes after incubating started and then the aliquot was mixed with 1 μL of 500 mM EDTA (pH 8.0) solution. This caused to terminate DNA degradation reaction in the reaction solution. Finally, each reaction solution containing EDTA was analyzed by electrophoresis. The gel used for electrophoresis was 15% polyacrylamide gel. Electrophoresis was carried out at 20 mA for 60 minutes. GelStar nucleic acid gel stain (manufactured by LONZA Japan) was used for a gel stain after electrophoresis. ImageQuant 350 (manufactured by GE Healthcare Japan) was used for analysis of stained gels. FIG. 7 is a photographic image showing the experimental result from electrophoresis in Example 7. FIG. 8 was a graph showing a relationship between time after incubating started and brightness amounts of λDNA bands which λDNA was not degraded.

As is obvious from FIGS. 7 and 8, in the case of within 60 minutes after incubation started, λDNA was degraded only by about 5%, while in the case of 20 hours after the incubation started, λDNA was degraded by about 30%.

The disclosure derived from the result in Example 7 is explained in the following items (i) to (iv).

(i) A method for extending primer DNA with telomerase, comprising the following steps of:

(a) mixing a solution containing telomerase and DNase with non-primer DNA not as a substrate for telomerase (e.g., λDNA) to obtain a mixed solution, wherein in the step (a), DNase starts degrading λDNA; and (b) extending primer DNA with the telomerase by adding primer DNA as a substrate for telomerase (e.g., TS primer) to the mixed solution during degradation of the non-primer DNA with the DNase after the step (a).

In the step (b), the DNase degrades non-primer DNA (e.g., λDNA) and therefore the amount of the DNase degrading the TS primer is reduced.

(ii) A method for measuring an activity degree of telomerase, comprising the following steps of:

(a) mixing a solution containing telomerase and DNase with non-primer DNA not as a substrate for telomerase (e.g., λDNA) to obtain a mixed solution, wherein in the step (a), DNase starts degrading λDNA;

(b) extending primer DNA with the telomerase by adding primer DNA as a substrate for telomerase (e.g., TS primer) to the mixed solution during degradation of the non-primer DNA with the DNase after the step (a), wherein, in the step (b), the DNase degrades non-primer DNA (e.g., λDNA) and therefore the amount of the DNase degrading the TS primer is reduced; and (c) determining an activity of telomerase based on an extension degree of the extended primer DNA in the step (b).

The step (c) desirably includes the steps of:

(c1) amplifying the extended primer DNA in the step (b) by PCR;

(c2) subjecting the amplified primer DNA in the step (c1) to electrophoresis; and (c3) determining an activity degree of telomerase based on the result from electrophoresis in the step (c2).

(iii) A method for extending primer DNA with telomerase, comprising the following steps of:

(a) preparing a mixed solution containing non-primer DNA not as a substrate for telomerase (e.g., λDNA) and primer DNA as a substrate for telomerase (e.g., TS primer), wherein, in the step (a), a reaction is not occurred; and (b) extending the primer DNA with the telomerase by adding a solution containing telomerase and DNase to the mixed solution while degrading the non-primer DNA with the DNase after the step (a).

In the step (b), the amount of DNase degrading primer DNA is reduced compared with the case of not using non-primer DNA.

(iv) A method for measuring an activity degree of telomerase, comprising the following steps of:

(a) preparing a mixed solution containing non-primer DNA not as a substrate for telomerase (e.g., λDNA) and primer DNA as a substrate for telomerase (e.g., TS primer), wherein, in the step (a), a reaction is not occurred;

(b) extending the primer DNA with the telomerase by adding a solution containing telomerase and DNase to the mixed solution while degrading the non-primer DNA with the DNase after the step (a), wherein, in the step (b), the amount of DNase degrading primer DNA is reduced compared with the case of not using non-primer DNA; and (c) determining an activity of telomerase based on an extension degree of the extended primer DNA in the step (b).

The step (c) desirably includes the steps of:

(c1) amplifying the extended primer DNA in the step (b) by PCR;

(c2) subjecting the amplified primer DNA in the step (c1) to electrophoresis; and (c3) determining an activity degree of telomerase based on the result from electrophoresis in the step (c2).

The measurement method of telomerase activity of the present disclosure is useful in technical fields such as biochemistry, biology and medical as a measurement method of telomerase activity with high accuracy and high quantitative capability.

What is claimed is:

1. A method for extending primer DNA with telomerase, the method comprising the steps of:
   (a) mixing non-primer DNA not as a substrate for telomerase with a solution containing contaminant DNase to provide a mixed solution, the non-primer DNA being selected to function as a substrate for the contaminant DNase; and
   (b) adding the primer DNA as a substrate for telomerase to the mixed solution to extend the primer DNA with the telomerase, while the non-primer DNA is being degraded by the DNase after the step (a).

2. The method according to claim 1,
   wherein the non-primer DNA is λDNA, plasmid DNA or M13DNA.

3. A method for measuring an activity degree of telomerase, the method comprising the steps of:
   (a) mixing a solution containing contaminant DNase with non-primer DNA not as a substrate for telomerase to provide a mixed solution, the non-primer DNA being selected to function as a substrate for the contaminant DNase;
   (b) adding primer DNA as a substrate for telomerase to the mixed solution to extend the primer DNA with the telomerase, while the non-primer DNA is being degraded by the contaminant DNase after the step (a); and
   (c) determining an activity of the telomerase based on an extension degree of the extended primer DNA in the step (b).

4. The method according to claim 3,
   wherein the step (c) comprises the steps of:
   (c1) amplifying the extended primer DNA in the step (b) by PCR;
   (c2) subjecting the amplified primer DNA in the step (c1) to electrophoresis; and
   (c3) determining an activity degree of the telomerase based on a result from the electrophoresis in the step (c2).

5. The method according to claim 3,
   wherein the non-primer DNA is λDNA, plasmid DNA or M13DNA.

6. A method for extending primer DNA with telomerase, the method comprising the steps of:
   (a) preparing a mixed solution containing non-primer DNA not as a substrate for telomerase and primer DNA as a substrate for telomerase, the non-primer DNA being selected to function as a substrate for contaminant DNase present in the solution; and
   (b) extending the primer DNA with the telomerase by adding a solution to the mixed solution while degrading the non-primer DNA with the DNase after the step (a).

7. The method according to claim 6,
   wherein the non-primer DNA is λDNA, plasmid DNA or M13DNA.

8. A method for measuring an activity degree of telomerase in a solution containing contaminant DNase, the method comprising the steps of:
   (a) preparing a mixed solution containing M13DNA and primer DNA as a substrate for telomerase;
   (b) extending the primer DNA with the telomerase by adding a solution to the mixed solution while degrading the M13DNA with the DNase after the step (a); and
   (c) determining an activity of the telomerase based on an extension degree of the extended primer DNA in the step (b).

9. The method according to claim 8,
   wherein the step (c) comprises the steps of:
   (c1) amplifying the extended primer DNA in the step (b) by PCR;
   (c2) subjecting the amplified primer DNA in the step (c1) to electrophoresis; and
   (c3) determining an activity degree of the telomerase based on a result from electrophoresis in the step (c2).

* * * * *

SEQUENCE LISTING

```
<160> NUMBER OF SEQ ID NOS: 2

<210> SEQ ID NO 1
<211> LENGTH: 11
<212> TYPE: RNA
<213> ORGANISM: Artificial Sequence
<220> FEATURE:
<223> OTHER INFORMATION: 46th to 56th RNA Sequence of Telomerase RNA

<400> SEQUENCE: 1
cuaacccuaa c                                                            11

<210> SEQ ID NO 2
<211> LENGTH: 18
<212> TYPE: DNA
<213> ORGANISM: Artificial Sequence
<220> FEATURE:
<223> OTHER INFORMATION: TS Primer
```

```
<400> SEQUENCE: 2
aatccgtcga gcagagtt                                                    18
```